United States Patent [19]

Humphries et al.

[11] Patent Number: 5,536,662
[45] Date of Patent: * Jul. 16, 1996

[54] CELL ASSAY DEVICE

[75] Inventors: Gillian M. K. Humphries, Los Altos; Donald L. Miller, Kensington; Jeffrey M. Libby, Cupertino; Henry L. Schwartz, Los Gatos, all of Calif.

[73] Assignee: Molecular Devices Corporation, Sunnyvale, Calif.

[*] Notice: The portion of the term of this patent subsequent to Apr. 14, 2009, has been disclaimed.

[21] Appl. No.: 161,198

[22] Filed: Dec. 2, 1993

Related U.S. Application Data

[63] Continuation of Ser. No. 836,991, Feb. 14, 1992, abandoned, which is a continuation of Ser. No. 532,571, Jun. 4, 1990, Pat. No. 5,104,804.

[51] Int. Cl.⁶ .................................................. C12M 1/34
[52] U.S. Cl. .................................. 435/287.1; 435/283.1; 435/287.4; 204/403
[58] Field of Search .................... 435/4, 29, 32, 435/39, 240, 241, 182, 284–286, 288, 291, 817, 311; 204/403, 409, 415, 153.12, 153.17

[56] References Cited

U.S. PATENT DOCUMENTS

| | | | |
|---|---|---|---|
| 3,591,480 | 7/1971 | Neff et al. | 204/403 |
| 3,616,409 | 10/1971 | Tosteson | 204/409 |
| 3,725,237 | 4/1973 | Matsuyama et al. | 204/409 |
| 3,737,379 | 6/1973 | Tosteson | 204/409 |
| 4,216,065 | 8/1980 | Rechanitz et al. | 204/403 |
| 4,686,190 | 8/1987 | Cramer et al. | 435/291 |
| 4,734,372 | 3/1988 | Rotman | 435/291 |
| 4,812,407 | 3/1989 | Buchmann et al. | 435/285 |
| 4,871,674 | 10/1989 | Matsui et al. | 435/285 |
| 4,911,794 | 3/1990 | Parce et al. | 435/817 |
| 4,950,379 | 8/1990 | Young et al. | 435/817 |
| 5,026,649 | 6/1991 | Lyman et al. | 435/284 |
| 5,104,804 | 4/1992 | Humphries et al. | 435/291 |
| 5,278,048 | 1/1994 | Parce et al. | 435/291 |

FOREIGN PATENT DOCUMENTS

| | | | |
|---|---|---|---|
| 0255223 | 2/1988 | European Pat. Off. | |
| 0244853 | 12/1985 | Japan | 435/291 |
| 1-265150 | 10/1989 | Japan | 204/403 |
| 0734280 | 5/1980 | U.S.S.R. | 435/284 |

OTHER PUBLICATIONS

Hafeman et al. "Light–Addressable Potentiometric Sensor for Biochemical Systems", Science, vol. 240 (May 1988) pp. 1182–1185.

Li et al. "Computer Aided Analysis for Biosensing and Screening", Biotechnology and Bioengineering, vol. 31 (1988) pp. 250–256.

Primary Examiner—William H. Beismer
Attorney, Agent, or Firm—Banner & Allegretti, Ltd.

[57] ABSTRACT

This invention encompasses porous microchambers which contain cells and permit liquid to flow in and out of the chamber while retaining cells within the chamber. These porous microchambers serve as disposable devices for placing cells in a microflowchamber so that properties of the cells within the porous microchamber can be measured.

1 Claim, 4 Drawing Sheets

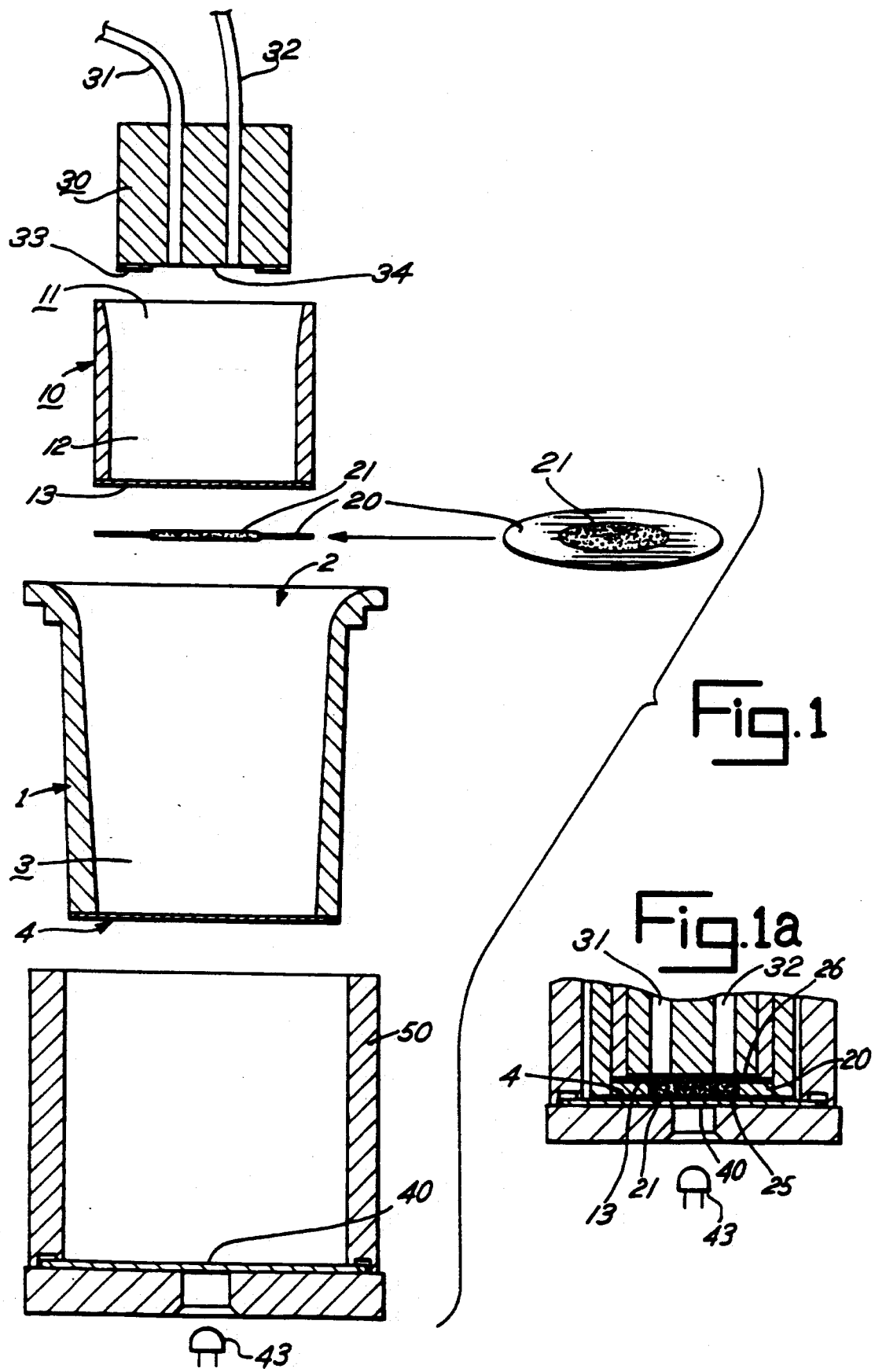

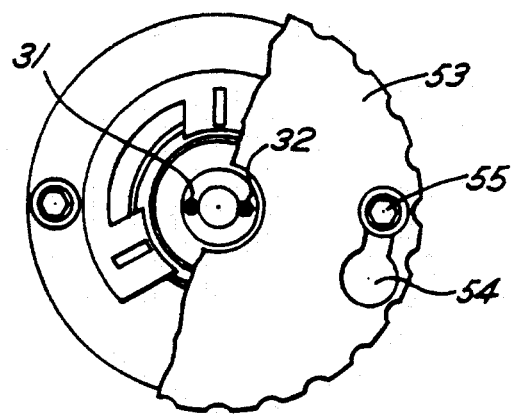
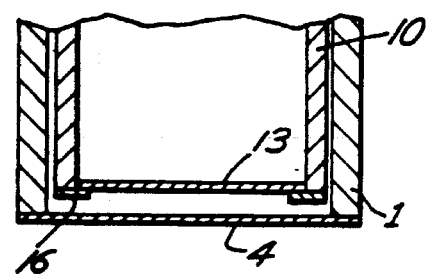
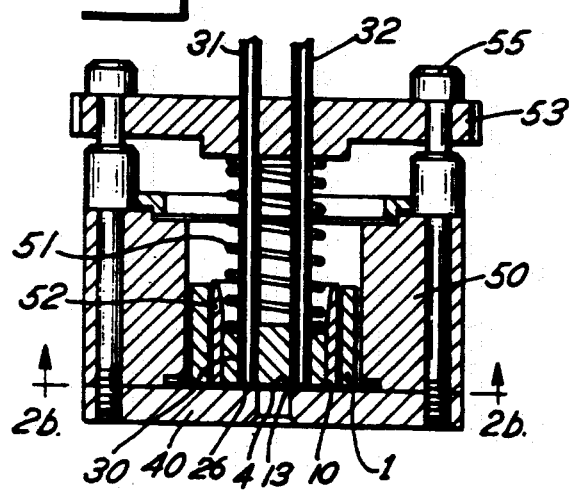
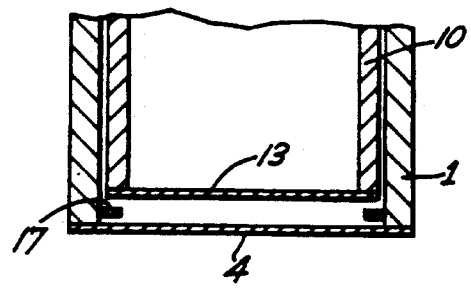
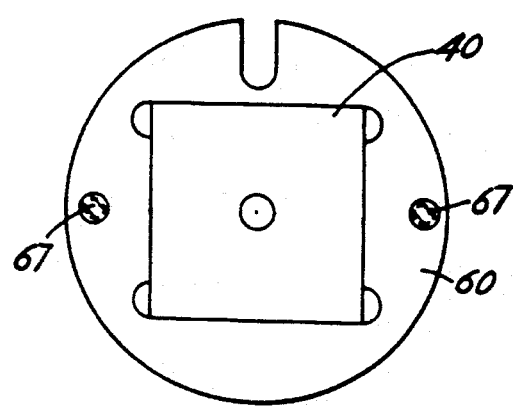

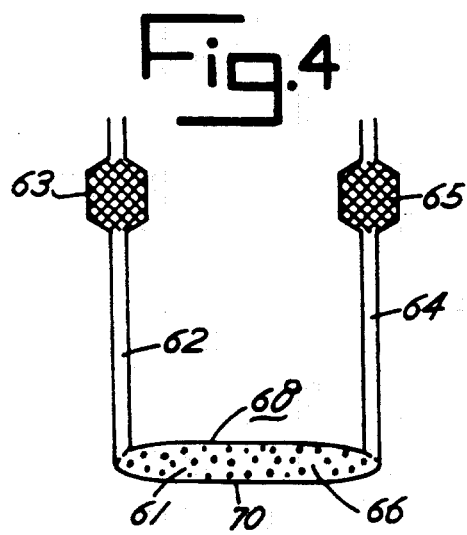
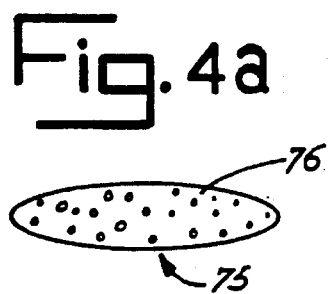
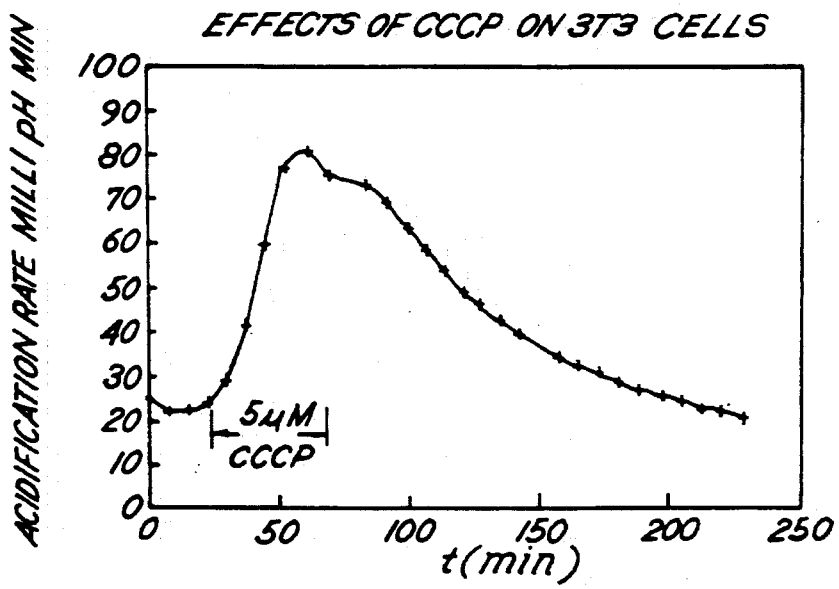
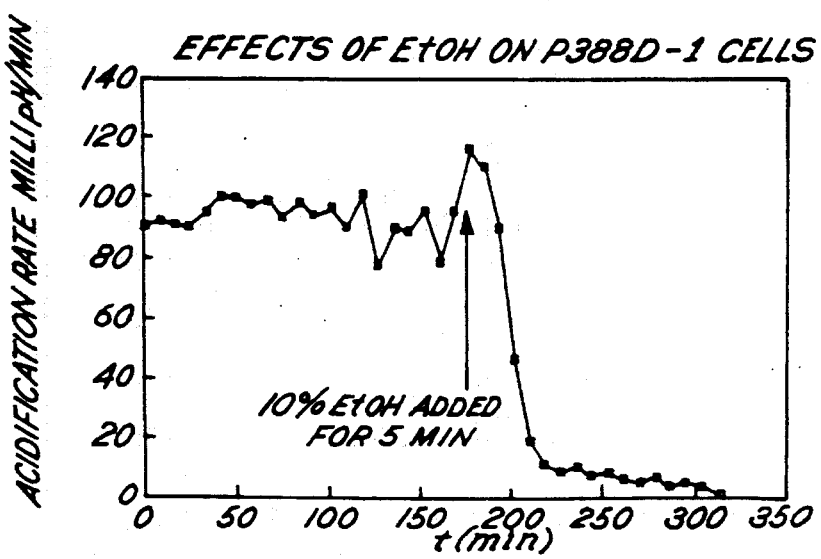

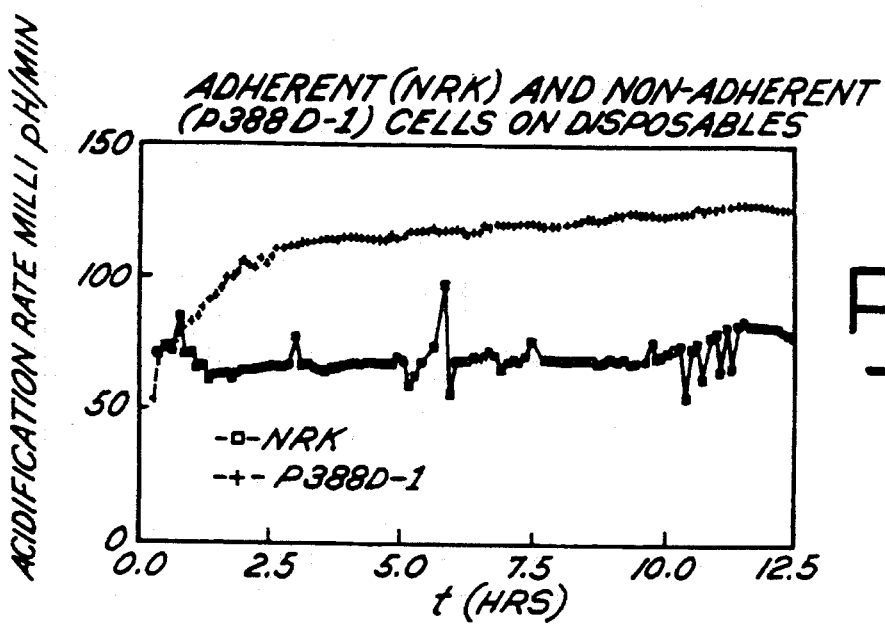
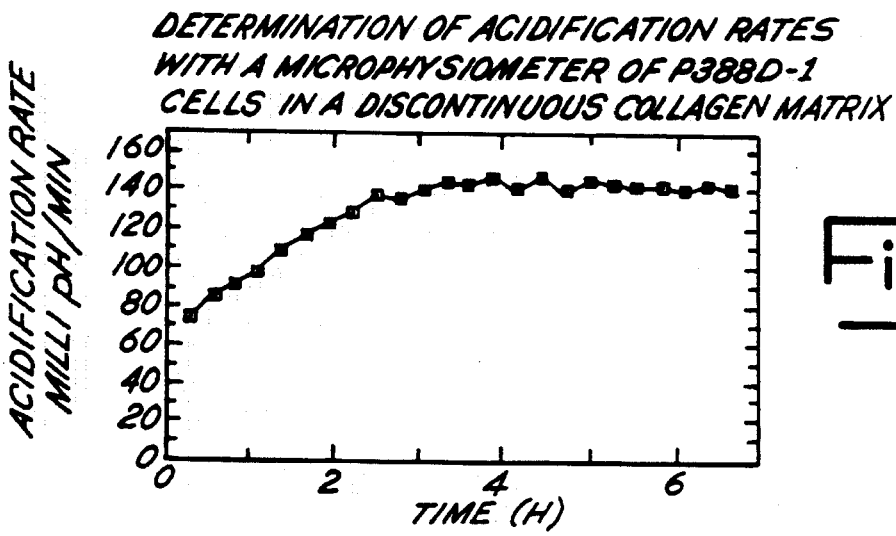
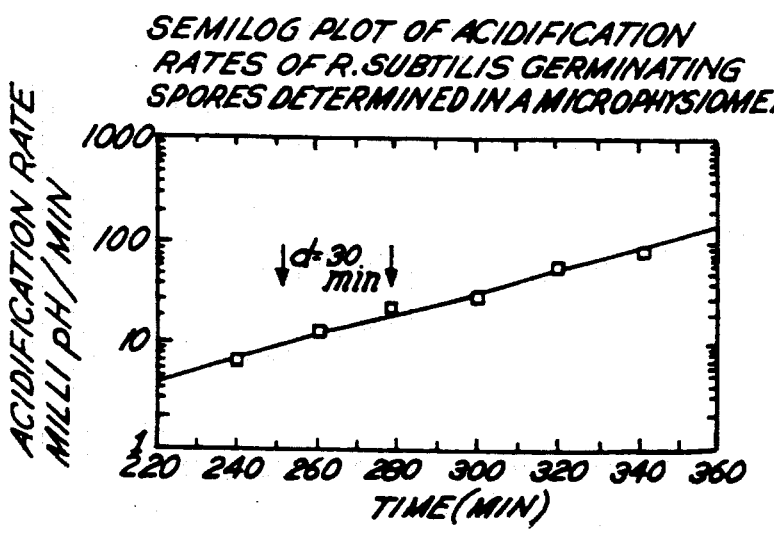

CELL ASSAY DEVICE

RELATED APPLICATION

This application is a continuation of application Ser. No. 07/836,991, filed Feb. 14, 1992, now abandoned, which is a continuation of application Ser. No. 07/532,571, filed Jun. 4, 1990, now U.S. Pat. No. 5,104,804, issued Apr. 14, 1992.

BACKGROUND OF THE INVENTION

1. Field of the Invention

This invention is in the field of microphysiometers and, in particular, it relates to single-use disposable devices and reagents, and reusable peripheral parts, used in conjunction with a microphysiometer.

2. Description of the Prior Art

The prior art describes cups which have a filter membrane on the bottom and such cups are usable for filtering and grouping cells on the inner surface of the membrane ("Selected Methods in Cellular Immunology", Edited by Barbara B. Mishell and Stanley M. Shiigi, University of California, Berkeley, Editorial Consultants: Claudia Henry and Robert I. Mishell, University of California, Berkeley, Published by W. H. Freeman and Company, San Francisco, Copyright 1980, pp. 37, 40, 43, 61, 62, 63 and 64). Also of interest are silicon electrodes for use in microflow cells described in U.S. Pat. Nos. 4,591,550; 4,737,464; 4,741,619; 4,704,353 and 4,519,890. These patents are incorporated herein by reference.

Further prior art takes the form of commercially-available single use vessels for the culture of living cells. In general, because of the extreme sensitivity of living cells to the chemical and physical nature of their environment (including potential problems with infection by bacteria, contamination by endotoxin or by cleaning solutions), it is preferable to use culture vessels that have been manufactured under carefully controlled conditions and then thrown away rather than cleaned and recycled. Although commercially-available single-use vessels take many forms, including bottles, tubes, and single or multiwell covered dishes, the closest commercially-available prior art items are all essentially manufactured versions of the design described in the first reference given in the previous paragraph (specifically pages 61, 62, 63, 64 of that reference). Manufacturers of such items include Costar Corp., Cambridge, Mass., (product name: Transwell) and Millipore Corp., Bedford, Mass., (product name: Millicell).

BRIEF DESCRIPTION OF THE DRAWINGS

FIG. 1 is a cross-sectional schematic of components of the device of example 1;

FIG. 1a is a cross-sectional schematic of the microflow-chamber;

FIG. 2 is a cross-sectional view of the device showing the spring loading mechanism;

FIG. 2a is a cut-away top plan view of 2;

FIG. 2b is a bottom plan view 2;

FIG. 3 is a cross-sectional view showing integral spacer means;

FIG. 3a is a cross-sectional view showing integral spacer means;

FIG. 4 is a schematic of a bacterial indicator device;

FIG. 4a is a capsule of porous membrane material containing cells;

FIG. 5 is the effect of carbonyl cyanide m-nitrophenyl-hydrazine (CCCP) on 3T3 cells;

FIG. 6 shows the effects of ethanol on P388D-1 cells; and

FIG. 7 shows continuous monitoring of adherent and non-adherent cells;

FIG. 8 is a plot of acidification rates verses time for P388D-1 cells in a discontinuous collagen matrix;

FIG. 9 is a semilog plot of acidification rates verses time.

SUMMARY OF THE INVENTION

This invention encompasses porous microchambers of which at least part of the chamber wall is constructed from a porous material such that fluids and agents contained therein can enter the porous microchamber when placed in a flowing stream, but cells cannot escape.

One embodiment of the invention provides for convenient assembly (or closure) of the microchamber, containing cells of choice, prior to use in the microphysiometer. In this embodiment, rigid inner and outer sleeves covered at one end with a porous membrane, together with spacing means, are fitted together such that when the inner sleeve is fully inserted in the outer sleeve, the membranes are separated by a spacing means. Thus, the spacing means and the inner and outer membrane form a microchamber having living cells trapped within. The sleeves are adapted for holding the microchamber containing the cells adjacent to a silicon electrode that forms one wall of a flat microflowchamber. Cells are retained within the internal cavity of the porous microchamber while liquid is permitted to flow through, above, between, and below the membranes and around the cells. (See FIG. 1). The principal direction of flow of the liquid is parallel to the plane of the membranes and the silicon surface. Changes in the media surrounding the cells (such as pH changes) can be measured by the silicon electrode. Design objectives include (a) maximizing cell volume/medium volume ratio to increase measurement sensitivity, (b) optimizing exchange rate of flowing liquid to flush out spent medium and/or introduce reagents, (c) minimizing the distance that measurable species such as protons must diffuse to reach the silicon electrode. The device of this invention provides a convenient disposable reagent for use in a microphysiometer of the type described in U.S. Ser. No. 04/694,469, now abandoned, assigned to the same assignee as this application and incorporated herein by reference.

In another embodiment of the invention, certain cells, such as bacterial spores, would be trapped between two membrane discs that are welded or stuck together at their edges to form a preassembled package that could be dropped into a microphysiometer flow chamber. Use of such a device would include, but not be limited to, validation of sterilization procedures; the preassembled spore package would be used as a biological indicator (BI) included in a load of items to be sterilized. In a further improvement of the BI for use in the microphysiometer, feed and waste lines would be firmly attached to the spore package, as well as filters to prevent entry of contaminating microorganisms from the feed line and the waste line exit. Thus, cells encapsulated in porous material to form a porous microchamber can be placed in the microflowchamber and advantageously studied in accord with this invention.

DETAILED DESCRIPTION OF THE INVENTION

Several embodiments of this invention are described with reference to FIG. 1. In its simplest embodiment outer sleeve 1 has an upper opening 2 and a lower opening 3 which is covered with porous membrane 4. An inner sleeve 10 has an upper opening 11 and a lower opening 12 which is covered with a porous membrane 13. Inner sleeve 10 fits within outer sleeve 1. A spacer means 20, in this instance a piece of plastic sheet material which defines an opening 21, fits into the outer sleeve. Thus, when the inner sleeve is inserted into the outer sleeve membranes 13 and 4 and the spacer means define a porous microchamber 25 in FIG. 1a. In operation a plunger 30 is inserted into the inner sleeve. Plunger 30 has an inlet 31 and an outlet 32 and when the plunger is tightly pressed against the membrane 13 a seal is formed by ridge 33 on the plunger. Liquid can flow from the inlet in 31 above, through, between, and below membranes 13 and 4 and the through outlet 32. A silicon sensor of the type described in U.S. Pat. Nos. 4,519,550, 4,737,464, 4,741,619, 4,704,353 and 4,519,890 is adjacent and parallel to the outer surface of membrane 4 so that changes in the solution caused by the cells, such as pH, can be detected by the sensor 40. After measurement the inner and outer sleeve containing the cells can be discarded. A light emitting diode 43 is positioned proximate an opening in the bottom of flow chamber casing 50 (FIGS. 1 and 1a).

In one embodiment spontaneously adhering cells are placed on the inner surface of membrane 4. In another embodiment the cells are deposited in a polymer matrix, such as a collagen sponge, in the opening 21 of the spacer means. The cells in the polymer matrix are then incorporated into the porous microchamber 25. This embodiment is primarily used with cells that do not spontaneously adhere to porous membranes. While in the embodiment illustrated in FIG. 1 the spacer means is a separately inserted disk, the spacer means can also be integral with the inner and outer sleeve. In a third embodiment, a mixture of non-adherent cells and a preparation of discontinuous matrix such as particles of collagen sponge with diameters typically 10–10000 times that of the cells they are to entrap, are co-centrifuged into the outer sleeve before insertion of the inner sleeve to form the chamber.

The porous membranes are made of biocompatible porous polymer material. A preferred material is a porous polycarbonate membrane. The pore size of this membrane can be selected for use with different cells. For example, a small pore size (0.45 micron or less) is suitable for use with bacteria, while a larger pore size (generally in the range 3–12 micron) is chosen for eukaryotic cells.

The inner and outer sleeve may have a variety of shapes, for example, they may be circular, oval, square or rectangular. A preferred shape because of flow pattern considerations is oval. The inner sleeve fits quite loosely into the outer sleeve. The sleeves are generally made of rigid polymer material such as polystyrene. It is important that the outer and inner sleeves in combination are specifically structured to bring the microchamber and, in particular, the outer surface of the membrane of the outer sleeve in intimate contact with the detecting electrode. It is also important that the plunger, together with the plunger ridge 33 and the spacer means form a seal to provide a leak tight compartment defining the microflowchamber 26 so that solution can be flowed in and out of the microflowchamber 26 by way of inlet 31 and outlet 32. Thus, the silicon electrode surface 40 forms one wall of the microflowchamber 26 and the bottom surface of the plunger 34 forms the top surface of the microflowchamber 26 within which a porous microchamber containing cells is removably placed. The microflowchamber 26 has dimensions of between 10 nanoliters and 10 microliters. Although for certain applications in which analysis of effluent from the chamber is desired and cells are trapped by a polymer matrix, longer volumes may be preferable as long as the cell larger volume/flow chamber volume can be kept high enough to attain sufficient pH change rate for measurement. The plunger is made of rigid, polymer materials and is spring loaded to ensure a seal on the outer edges of the membranes. The inner and outer sleeves and the spacer with or without the cell trapping polymer matrix are intended to be disposable items.

FIG. 2 illustrates a spring loading mechanism for maintaining the plunger in a position to form and seal the microflowchamber. The flow chamber casing 50 receives the outer sleeve 1. The inner sleeve 10 fits within the outer sleeve 1 and the plunger 30 fits within the inner sleeve 10 sufficiently loosely that air readily exits from between the pieces when they are being positioned. Tubing 31 and 32 deliver solution through the plunger to and from the microflowchamber 26. Spring 51 is attached to the top 52 of the plunger and the plunger retainer 53. The plunger retainer means 53 has an opening 54 for retaining the plunger in the down position by engaging post 55. A top view is shown in FIG. 2a. FIG. 2b shows a bottom plate 60 and silicon electrode 40. Hole 67 provides for locking plate 60 to the flow chamber casing 50.

Turning plunger retainer 53 counter clockwise releases the plunger retainer and the plunger can be removed.

FIG. 3, and 3a illustrate other types of integral spacer means. In FIG. 3 an integrally molded spacer 16 is on the bottom opening inner sleeve 10 before membrane 13. In FIG. 3a the spacer 17 is integrally molded on the bottom opening of sleeve 1 with membrane 4 on the outside of 17 and membrane 13 on sleeve 10 on the inside of the spacer. Cells are placed on the inner surface of the membrane 4 of the outer sleeve 1 and the spacer 20 is inserted in the outer sleeve. The inner sleeve 16 is inserted to press against the spacer 20. The plunger 30 is pressed into the inner sleeve to form a seal between the spacer and the membranes and define microflowchamber 26. The membrane 4 rests on the silicon electrode 40 and fluid is pumped over the cells. Various cell affecting agents are contained in the fluid and the effects of those agents on the cells is measured by silicon electrode 40. The small volume of the microflowchamber provides for extremely sensitive or responsive measurements.

FIG. 4 illustrates details of a porous microchamber intended for use as a Biological Indicator. In FIG. 4 spores 61 are trapped between upper 68 and lower 70 porous membranes and a feed line or inlet 62 with in-line filter 63 and a waste line or outlet 64 with in-line filter 65. The filter prevents bacteria from entering the microchamber 66 and is made from a material such as nitrocellulose or polycarbonate mesh material having pore size of 0.2–0.45 microns, typically. In this embodiment liquid can be flowed through feed line 62 through the microchamber 66 and out the waste line.

Spores are typically of the genus bacillus, such as *bacillus subtillis*, ATCC #9372, subspecies niger. FIG. 4a illustrates a capsule of porous material 75 containing cells 76. This porous capsule fits in the microflowchamber. The invention is further illustrated by the following examples.

EXAMPLE 1

Effects of Exogenous Cell-Affecting Agent on the Metabolism of Adherent Cells in a Single Use Cell Assay Device as Measured with the Microphysiometer Adherent cells, sometimes referred to as anchorage-dependent cells, generally must be attached to a biocompatible surface in order to maintain stable metabolic rates and increase in numbers. Adherent cell lines have been used for a wide variety of studies, including toxicological, pharmacological and environmental applications. In order to study whether adherent cells could be used in a single use cell assay device designed for the microphysiometer, the following procedure was performed. Outer sleeves 1 were placed in a 12-well tissue culture plate and Dulbecco's modification of Eagles medium (DME) containing 5% fetal bovine serum was added to the wells to 50% of capacity. The sleeves were seeded with mouse fibroblast 3T3 cells (an adherent cell line) and the entire plate was incubated at 37° C. in 5% $CO_2$ for 2 or more days. During this time the cells settled to the bottom of the sleeves and attached to the porous membranes, whereupon they were allowed to grow to approximately 70% confluency. At that time each outer sleeve was removed from the plate and spacer means 20 and inner sleeve 10 were placed on top of the layer of living cells. This entire assembly was then placed inside the flow chamber casing 50.

It was important during assembly to prevent air bubbles from being introduced into the flow chamber. This is accomplished by the following means: (1) a small amount of medium must be present on top of the silicon electrode 40 so that when sleeve 1 is placed on top no air is trapped between the two surfaces; (2) a small amount of medium must be present on top of the layer of cells and the spacer means on top of membrane 4, and membrane 13 must be dry before inserting the inner sleeve 10 into outer sleeve 1—care must be taken to visually ensure that there are no bubbles trapped between the membranes or below the bottom membrane 4; (3) the inlet line 31 must be filled with medium and a small drop of medium should suspend under the plunger surface 34 before introduction of the plunger assembly into the inner sleeve. Additional components were assembled as described in the text and shown in FIGS. 1 and 2, and the whole placed within the microphysiometer and maintained at 37° C. DME without bicarbonate (having a buffer capacity of approximately 2 mM) was then perfused into the chamber and acidification rates were measured periodically as described by Parce et al. (*Science* 246, 243 (1989)). During the indicated period the DME was supplemented with the metabolic uncoupler carbonyl cyanide m-nitrophenylhydrazine (CCCP; 5 micromolar M). The rate of medium acidification increased while the cells were exposed and then returned to the original acidification rate after replacement of the CCCP-containing perfusion medium with the original medium (See FIG. 5).

EXAMPLE 2

Immunobilization and Monitoring of the Metabolism of Non-adherent Cells in a Continuous Polymer Matrix Non-adherent cells (also known as anchorage-independent cells) generally do not become anchored to adjacent surfaces. Nevertheless, it may be desirable to use a microphysiometer to monitor the metabolism of of some of these types of cells for toxicological, pharmacological, environmental, etc., purposes. In initial experiments in which non-adherent cells were trapped between two membranes as described in Example 1, reproducible acidification was not observed and subsequent studies revealed that the cells were swept to the sides of the porous microchamber away from the central detector by the movement of fluid through this volume. In order to prevent this loss of non-adherent cells due to convective movement of fluid, some restriction of cell movement was deemed necessary.

A number of biocompatible sponge-like materials have been made commercially available for use as hemostatic agents. These materials, include, but are not limited to, collagen, polyvinyl alcohol and polyurethane. When applied to a surgical wound, these materials prevent the deposition of healing tissue. The tortuous network and proven biocompatible nature of these materials might allow them to serve as cell immobilization matrices, and thus some of these materials were tested for their ability to immobilize non-adherent cells within the microphysiometer. To accomplish this, a spacer means 20 was placed within an outer sleeve 1 containing a 5 pore polycarbonate membrane. Into the center hole of the spacer means a 6 mm diameter disk of polymer matrix, approximately 150 microns thick, was placed. The outer sleeve 1 and polymer matrix were placed within a well of a 12-well microtiter plate. For experiments with mammalian cells, a spacer means 20 was inserted in the outer sleeve prior to addition of the polymer matrix. One ml of a suspension containing either P388D-1 cells (non-adherent mammalian cells; approximately $10^7$ cells/ml) or *Saccharomyces cereviseae* (non-adherent yeast cells; approximately $10^7$ cells/ml) was pipetted into the outer sleeve. The microplate was then centrifuged at 400×g for 5 min., after which an inner sleeve 10 was placed within the outer sleeve and thus a second membrane was located above the cells trapped within the polymer matrix. The inner and outer sleeves, spacer means (when present), polymer matrix and cells were inserted into the flow chamber casing 50 and acidification rates of the cells were determined as described in Example 1. With the mammalian cell line stable metabolic rates were achieved for the duration of the experiment. In the yeast experiment the rates of acidification determined with the microphysiometer increased with time, indicating an increase in cell number within the microflowchamber for the duration of the experiment. Both of these experiments suggest that the cells were properly immobilized and their metabolism not adversely affected by the immobilization procedure or the microphysiometer environment.

EXAMPLE 3

Effects of Ethanol on the Metabolism of a Population of Non-adherent Cells

P388D-1 cells were centrifuged into a polymer matrix and their metabolism monitored with a microphysiometer as described in Example 2. After a period of adjustment to the microphysiometer environment during which time the rates of acidification of the cells' environments stabilized, the DME with 5% fetal bovine serum was replaced with DME containing 5% fetal bovine serum and 10% ethanol for a period of 5 min. Following the exposure to this potentially harmful formulation, the medium lacking ethanol was reintroduced into the microphysiometer and used to flush out the ethanol-containing medium. The metabolism of the P388D-1 cells was continuously monitored during the medium exchange. As can be seen in FIG. 6, this concentration of ethanol suppressed the metabolism of the cells, and this effect was not reversed by the removal of ethanol from the perfusion medium, suggesting that irreversible damage may have been done to the cells immobilized in the microphysiometer.

EXAMPLE 4

Long-term Continuous Monitoring of Both Adherent and Non-Adherent Cell Metabolism Non-adherent (P388D-1) and adherent (NRK) cells were placed in each of two disposable cell assay devices in the manners described in Examples 1 and 2 and placed within each of two cell chambers in a microphysiometer. The respective acidification rates of the two populations were measured for a period of over 12 hours while DME containing 5% fetal bovine serum was perfused through the cell chambers. FIG. 7 represents a plot of the acidification rates of these cell populations, both of which demonstrated stable rates for the duration of the experiment. The non-adherent cell population required a period of adjustment to the microphysiometer environment (approximately 2.5 h), during which the acidification rate for this population increased rapidly. This was followed by a long period of less dramatic increase in the rate of acidification, said state occurring for the remainder of the experiment.

EXAMPLE 5

Immobilization of Non-adherent Cells and Continuous Monitoring of Metabolism in a Discontinuous Matrix A polymer matrix which would form around non-adherent cells and thus immobilize them would eliminate the need to manufacture and position disks of precast polymer matrix. In order to test this concept, the procedure described in Example 2 was performed with the following modification. No precast polymer matrix was inserted into the spacer means 20. An collagen hemostatic sponge (Collastat, Vitaphore Corp., Chicago, Ill.) was suspended in phosphate-buffered saline solution pH 7.2) and finely chopped in a blender for six 3 sec. cycles. A volume (0.5 ml) of this suspension, which consisted of particles of collagen matrix of various sizes, mostly in the range of 0.2 to 1.0 mm diameter and representing about 0.5% (v/v) of the suspension, was mixed with 0.5 ml of a P388D-1 cell suspension (approximately $10^7$ cells/ml). The cell/polymer suspension was centrifuged at 400×g for 5 min. into the outer sleeve 1 with a spacer means 20; an inner sleeve 10 was added and this assembly was inserted into the flow chamber casing 50. The metabolism of the cells as indicated by the rate at which they acidified their environment was monitored as described in Example 1. After a period of acclimation to the microphysiometer environment, stable rates of acidification were measured for the duration of the experiment (FIG. 8). These results demonstrate that the discontinuous matrix used in this experiment did immobilize the non-adherent cells and that cellular metabolism was apparently not adversely affected by this procedure. Such a discontinuous matrix preparation may thus be appropriate for determining the effects of cell-affecting agents as described in Example 3.

EXAMPLE 6

Monitoring of Bacterial Growth and Metabolism in a Microphysiometer

In order to measure the rate of acidification of the microflowchamber environment by a bacterial population, a number of modifications to the experimental and single-use element design described in Example 1 were made. A suspension of *Bacillus subtilis* endospores which had been enumerated with a Petroff-Hauser direct counting chamber was centrifuged into an outer sleeve 1 with a spacer means 20. The suspension had been diluted to a density so that aprpoximately 250 endospores would be present in the microflowchamber when the microflowchamber was completely assembled. No polymer matrix was present, the lower membrane 4 had a pore size of 0.4 micron and the membrane above the endospores 13 had a pore size of 0.22 micron. Instead of DME with 5% fetal bovine serum, a complex bacteriological nutrient medium was substituted and the cells were incubated at 27° C. in the microphysiometer. This example provides evidence that the invention has utility in the field of validation of desterilization procedures when used as a biological indicator. No discernible metabolic rate could be observed until approximately four hours after the experiment began, after which a rapid increase in acidification was seen. From a semi-log plot of these rates a determination of the doubling time of *B. subtilis* in the microphysiometer could be determined (FIG. 9).

What is claimed is:
1. A device for removably placing cells in a microflowchamber of a microphysiometer comprising:
   (a) an outer sleeve having a top and bottom opening wherein the bottom opening of the outer sleeve is covered with a porous membrane; and
   (b) an inner sleeve fitting within the outer sleeve and having a top and bottom opening wherein the bottom opening of said inner sleeve is covered with a porous membrane which together with the outer sleeve and the porous membrane of the outer sleeve define a porous microchamber capable of fitting within the microflowchamber wherein cells are maintained in the porous microchamber when liquid flows through or above or between or below the porous membranes and wherein the microflowchamber has a volume of between 10 nanoliters and 10 microliters.

* * * * *